(12) United States Patent
Rand

(10) Patent No.: US 11,712,549 B2
(45) Date of Patent: Aug. 1, 2023

(54) ANTI-CLOGGING AND ANTI-ADHESIVE MICRO-CAPILLARY NEEDLE WITH ENHANCED TIP VISIBILITY

(71) Applicant: Kinneret Rand, Rockville, MD (US)

(72) Inventor: Kinneret Rand, Rockville, MD (US)

(*) Notice: Subject to any disclaimer, the term of this patent is extended or adjusted under 35 U.S.C. 154(b) by 672 days.

(21) Appl. No.: 16/456,695

(22) Filed: Jun. 28, 2019

(65) Prior Publication Data

US 2020/0001063 A1 Jan. 2, 2020

Related U.S. Application Data

(60) Provisional application No. 62/691,029, filed on Jun. 28, 2018.

(51) Int. Cl.
*A61M 37/00* (2006.01)
*B33Y 80/00* (2015.01)

(52) U.S. Cl.
CPC . *A61M 37/0015* (2013.01); *A61M 2037/0053* (2013.01); *B33Y 80/00* (2014.12); *B81B 2201/055* (2013.01); *B81B 2201/057* (2013.01)

(58) Field of Classification Search
CPC ...... A61M 37/0015; A61M 2037/0023; A61M 2037/003; A61M 2037/0046
See application file for complete search history.

(56) References Cited

U.S. PATENT DOCUMENTS

| 4,252,903 | A | 2/1981 | Kallies |
| 5,407,431 | A | 4/1995 | Botich et al. |
| 6,334,856 | B1 | 1/2002 | Allen et al. |

(Continued)

FOREIGN PATENT DOCUMENTS

| EP | 3037124 A1 * | 6/2016 |
| KR | 1020140031943 | 3/2014 |

(Continued)

OTHER PUBLICATIONS

International Search Report and the Written Opinion, PCT/US2019/039835, dated Aug. 27, 2019, 8 pages.

(Continued)

*Primary Examiner* — Courtney B Fredrickson
(74) *Attorney, Agent, or Firm* — Edell, Shapiro & Finnan, LLC

(57) ABSTRACT

An object of the present invention is to provide an anti-adhesive/anti-clogging and/or color marked/tinted micro-capillary tube (microtube), microneedle, or micropipette. Typically, the color/tint will be selected such that the tip of the microneedle or micropipette is in contrast (e.g., visually) to the biological material. The tint/color may be selected to contrast the stained biological material. In some aspects, the color mark comprises nanoparticles that are modified by adding a non-adhesive coating/material that minimizes protein adhesion/adsorption. The microtubes and/or micropipettes may be treated with an anti-clogging reagent and an anti-adhesive reagent to prevent or reduce clogging and adhesion of the micropipette or microneedle to biological materials. The microtubes and/or micropipettes may be formed using additive printing processes and additive manufacturing techniques or from micropipette and microneedle pullers.

13 Claims, 9 Drawing Sheets

(56) References Cited

U.S. PATENT DOCUMENTS

| | | | |
|---|---|---|---|
| 6,547,764 | B2 | 4/2003 | Larsen et al. |
| 6,716,192 | B1 | 4/2004 | Orosz, Jr. |
| 6,796,976 | B1 * | 9/2004 | Chin .................. A61M 25/0662 |
| | | | 604/533 |
| 8,608,697 | B2 | 12/2013 | Tran et al. |
| 8,708,966 | B2 | 4/2014 | Allen et al. |
| 9,462,969 | B2 | 10/2016 | Gao et al. |
| 2005/0245895 | A1 | 11/2005 | Haider et al. |
| 2006/0052766 | A1 | 3/2006 | Patel |
| 2007/0048350 | A1 | 3/2007 | Falotico et al. |
| 2007/0100279 | A1 * | 5/2007 | Bates .................... A61L 29/126 |
| | | | 977/700 |
| 2007/0179455 | A1 | 8/2007 | Geliebter et al. |
| 2008/0051695 | A1 * | 2/2008 | Xu .................... A61M 37/0015 |
| | | | 604/22 |
| 2009/0318833 | A1 * | 12/2009 | Lim ...................... A61M 5/329 |
| | | | 264/220 |
| 2010/0121307 | A1 * | 5/2010 | Lockard ............ A61M 37/0015 |
| | | | 604/117 |
| 2010/0196435 | A1 | 8/2010 | Freeman et al. |
| 2011/0208157 | A1 | 8/2011 | Geliebter et al. |
| 2012/0156302 | A1 | 6/2012 | Tanahashi et al. |
| 2013/0006147 | A1 * | 1/2013 | Fukuda ............ A61B 5/150458 |
| | | | 600/573 |
| 2015/0173883 | A1 | 6/2015 | Ingber et al. |
| 2016/0006928 | A1 | 1/2016 | Gibbons et al. |
| 2016/0158449 | A1 | 6/2016 | Limaye et al. |
| 2020/0330016 | A1 * | 10/2020 | Espina Perez ... A61B 5/150083 |

FOREIGN PATENT DOCUMENTS

| | | | | |
|---|---|---|---|---|
| WO | 2007012114 | A1 | 2/2007 | |
| WO | WO-2007042818 | A1 * | 4/2007 | ........ A61M 37/0015 |
| WO | 2010051551 | A1 | 5/2010 | |
| WO | 2012158631 | A2 | 11/2012 | |
| WO | 2014157164 | A1 | 10/2014 | |
| WO | WO-2017100480 | A1 * | 6/2017 | ......... A61B 5/14532 |

OTHER PUBLICATIONS

Kinneret Rand, SeeTrue Technology.mp4, URL: https://www.youtube.com/watch?v=mWHu9sw82iM, May 21, 2018, 3 pages.

Supplementary European Search Report, EP19825131, dated Mar. 10, 2022, 9 pages.

Guo et al., "Novel Surface engineered Micro-needles towards Bio-analytical Applications", 2016 IEEE International Conference, 5 pages.

* cited by examiner

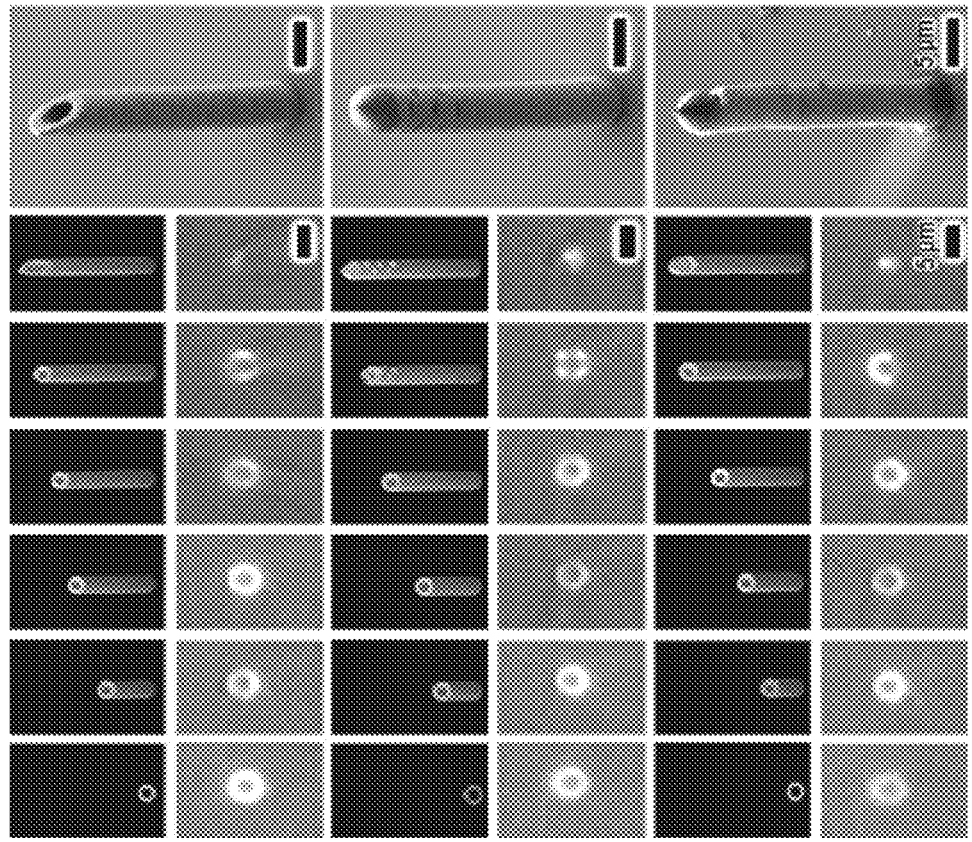
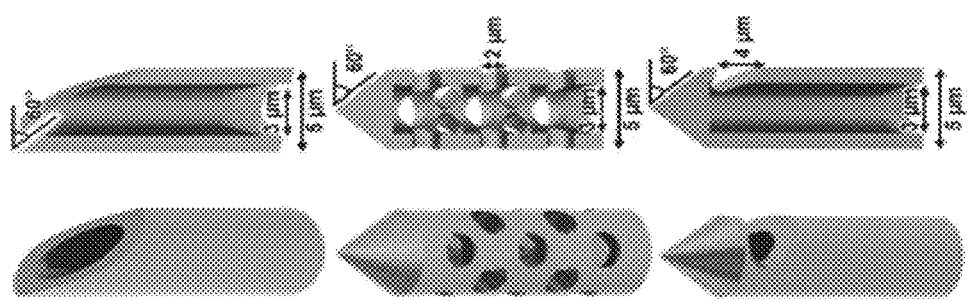

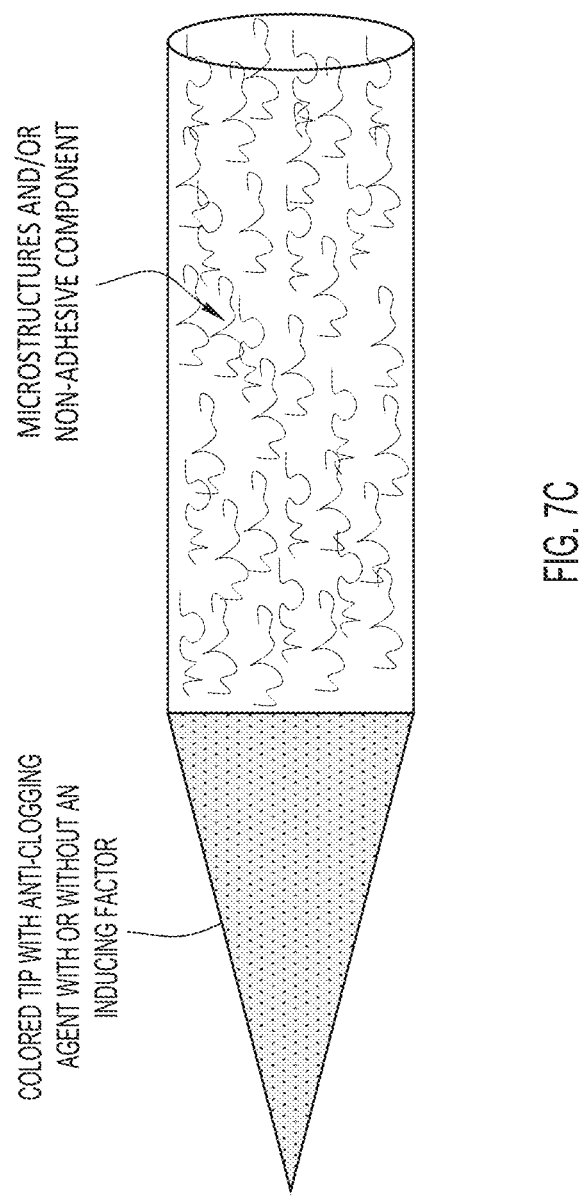

ANTI-CLOGGING AND ANTI-ADHESIVE MICRO-CAPILLARY NEEDLE WITH ENHANCED TIP VISIBILITY

CROSS REFERENCE TO RELATED APPLICATIONS

This application claims the benefit of U.S. Provisional Application No. 62/691,029, filed on Jun. 28, 2018, which is being incorporated by reference herein in its entirety.

BACKGROUND

Field of the Invention

The field of the invention relates to micro-capillary pipettes and micro-capillary needles, and in particular, to micro-capillary pipettes and micro-capillary needles that provide improved visibility and contrast relative to a biologic material, with non-adhesive and non-clogging properties.

Description of the Related Art

Micro-capillary needles (microneedles) and micro-capillary pipettes (micropipettes) are used in a wide variety of medical and scientific applications. For example, microneedles are used in microinjection, which is an in vitro technique for genetic manipulation. Using microinjection, a clear glass microneedle may be inserted into a biological target (e.g., such as a cell, tissue, etc.) to inject foreign materials (e.g., RNA and DNA, antibodies, proteins, Morpholino oligonucleotides, dyes, antisense RNA, kinases, histochemical markers (e.g., horseradish peroxidase or *lucifer* yellow, etc.), cells, metabolites, microbeads, ions, genes, etc.) into the target. However, microinjection remains inefficient for a variety of reasons, including suboptimal microneedle design and manufacturing practices, which have remained essentially unchanged since inception of this technology.

Industry standard microneedles (ISN), as shown in FIG. 1, are typically generated by a process that uses an industry standard pipette puller, in which ends of a hollow clear glass capillary tube are connected to the pipette puller. The pipette puller applies outward force, along a horizontal axis, to each end of the glass tube. By positioning a heating source near the middle of the capillary tube, the glass deforms under heat and force, thereby producing a finely tapered conical needle tip, for example, with an inner tip diameter ranging from about 0.2 µm to 10 µm. Microneedles with larger inner tip diameters may be formed as well.

However, this ISN design contributes to four main microinjection technique challenges. First, transparency of the needle creates low contrast visibility in vitro, making it difficult for a user to view and track the needle tip during insertion into the biological target/object. As shown in FIGS. 2A-2C, a user does not know the precise location of the tip of the needle inside the object to be injected. FIGS. 2A-2C show various experiments in which a holding pipette positions a mouse oocyte, with a capillary needle inside the oocyte. As the needle and the injected object are not both in the same focal plane, it is difficult to see the position of the needle. FIG. 2B appears to have slightly better focus, but is still difficult to visualize. In addition, it is difficult to align the tip of microneedle with the outside of the object to reach a precise penetration point. This imprecision and lack of visibility may cause a user to contact the needle tip with a hard surface which may cause needle breakage as the needle tip is typically only a few µm wide. Accordingly, locating intracellular targets is difficult, and further, optimizing the relationship between injection force and cell deformation to successfully deliver the material to the desired location in the object is challenging.

Second, cytoplasmic material or other components of the biological target may adhere, for example, via protein and lipid adsorption, to the glass tip resulting in clogging of the needle, which may lead to obstructed or complete blockage of the microneedle tip. Accordingly, the volume of injected material in an early injection trial using an unclogged needle tip may be significantly different from the volume of injected material delivered by the same needle tip, which may be partially clogged, in a later injection trial. In other aspects, biological components may adhere to the needle tip, resulting in cellular debris clumps surrounding the needle tip that reduce or block fluid flow. This may lead to rupture of the cell membrane and lysing of the cell when the microneedle tip is withdrawn.

Third, creating the needle tip opening is usually a manual process made by the microinjection practitioner using a sharp object like forceps. This manual process generates microneedles with variable inner diameters. For example, a first microneedle may have an inner tip diameter of 3 µm, a second microneedle may have an inner tip diameter of 4 µm, and a third microneedle may have an inner tip diameter of 2 µm, even when generated by the same practitioner under similar conditions. Given that this is a variable process, microneedles with tips of variable diameters are produced, which may add complexity and variability into the experiments if performed with microneedles of different sizes. For example, in the event that a microneedle becomes blocked mid-procedure, the blocked microneedle is replaced with a new microneedle, which may introduce volume/calibration inconsistencies into the experiments and may involve time and labor-intensive calibration procedures for each new needle used during the course of experimentation.

Fourth, injected cells can adhere to the inner walls of the glass capillary needle leading to costly injected material loss (e.g., sperm, human oocyte, etc.).

Accordingly, conventional microneedles have a variety of drawbacks, including limited visibility, clogging, variability of tip diameter, adherence of biological components, and breakage. In some cases, the microneedle may be the most error prone component of a microinjection system or other micro-capillary system.

SUMMARY

An object of the present invention is to provide a color marked/tinted micro-capillary tube (microtube), microneedle, or micropipette. In some aspects, a non-adhesive or non-clogging reagent/material is present along the interior and exterior surface of the microtube, microneedle, or micropipette. In general, a reagent may include any molecule, compound, coating, solution, material, etc. associated with a specific property, e.g., anti-clogging or anti-adhesion. Typically, the color/tint will be selected such that the tip of the microneedle or micropipette is in contrast (e.g., visually) to the biological material. The tint/color may be selected to highly contrast the biological material.

In some aspects, the non-adhesive reagent/material is added to the tip independently from the color mark. For example, the non-adhesive reagent/material may be added to the tip followed by the color mark or vice-versa. This approach produces a color marked tip resistant to adhesion and clogging that is easily visualized under a microscope.

In other aspects, the non-clogging reagent/material that minimizes protein adhesion/adsorption may be modified such that it is crosslinked to nanoparticles or other reagents that provide a color mark. This ensures a uniform and durable coating with the desired properties.

In other aspects, the color marking reagent may comprise dopants that have been added to the glass capillary/tip. In this example, transition metals that produce color may be added to the glass surface or the glass capillaries may be fabricated with the dopants, such that the dopants are embedded in the material of the glass. The non-adhesive coating/material may be added to the tip followed by the color marking reagent or vice-versa.

Non-adhesive reagents may include polymers which bind to the glass surface and render the glass surface negatively charged, such as polyethylene glycol (PEG). In other aspects, non-adhesive reagents may include copolymers.

The microtubes and/or micropipettes may be formed using additive printing processes and additive manufacturing technologies such as two-photon direct laser writing (DLW). For example, the tips may be fabricated by 3D printing, which offers substantial flexibility and design in terms of available shapes and color markings. For example, molecules which provide color marking and anti-adhesive/color marking properties may be added to the liquid polymeric solutions that undergo polymerization during printing of the 3D tip structure.

In other aspects, a micropipette or microneedle puller may be used to generate a pair of tips, which are then treated with one or more component(s) to provide desired color marking and anti-adherence/anti-clogging properties.

Methods are also provided for using the tips in any therapeutic or experimental biological system in which biological cells are injected or manipulated by micropipettes and microneedles.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

FIGS. 6A-6I show preliminary DLW results for representative microneedle tips. FIGS. 6A-6D correspond to conventional (control) designs, FIGS. 6E-6H correspond to multiple small side-ports designs, and FIGS. 6I-6L) correspond to single side-port designs. Also shown are conceptual illustrations (6A, 6E, and 6I), CAM simulations (6B, 6F, and 6J) and brightfield micrographs (6C, 6G, 6K) of the DLW process, and SEM micrographs (6D, 6H, 6L) of fabricated microneedle tips corresponding to each design.

FIG. 7C is a schematic of a microneedle, wherein microstructures are present in the interior of the tube region. The non-adhesive component is optionally present in the interior of the tube region as well as the tip region. The tip, in addition to containing the color marking reagent, may include an anti-clogging reagent on its exterior surface, and may also optionally include an inducing factor on the exterior surface. The inducing factor may induce an activity of a cell, such as motility, growth, etc. The inducing factor may be independently attached to the microneedle surface or may be conjugated to the anti-clogging reagent or color marking reagent.

DETAILED DESCRIPTION

An object of the present invention is to provide a color marked/tinted microtube, microneedle, or micropipette. Typically, the color/tint will be selected such that the tip of the microneedle or micropipette is in contrast (e.g., visually) to the biological material. In an aspect, the color marked microtube, microneedle, or micropipette may be coated with a non-adhesive and non-clogging reagent. These features are further described as follows.

Figure 1:
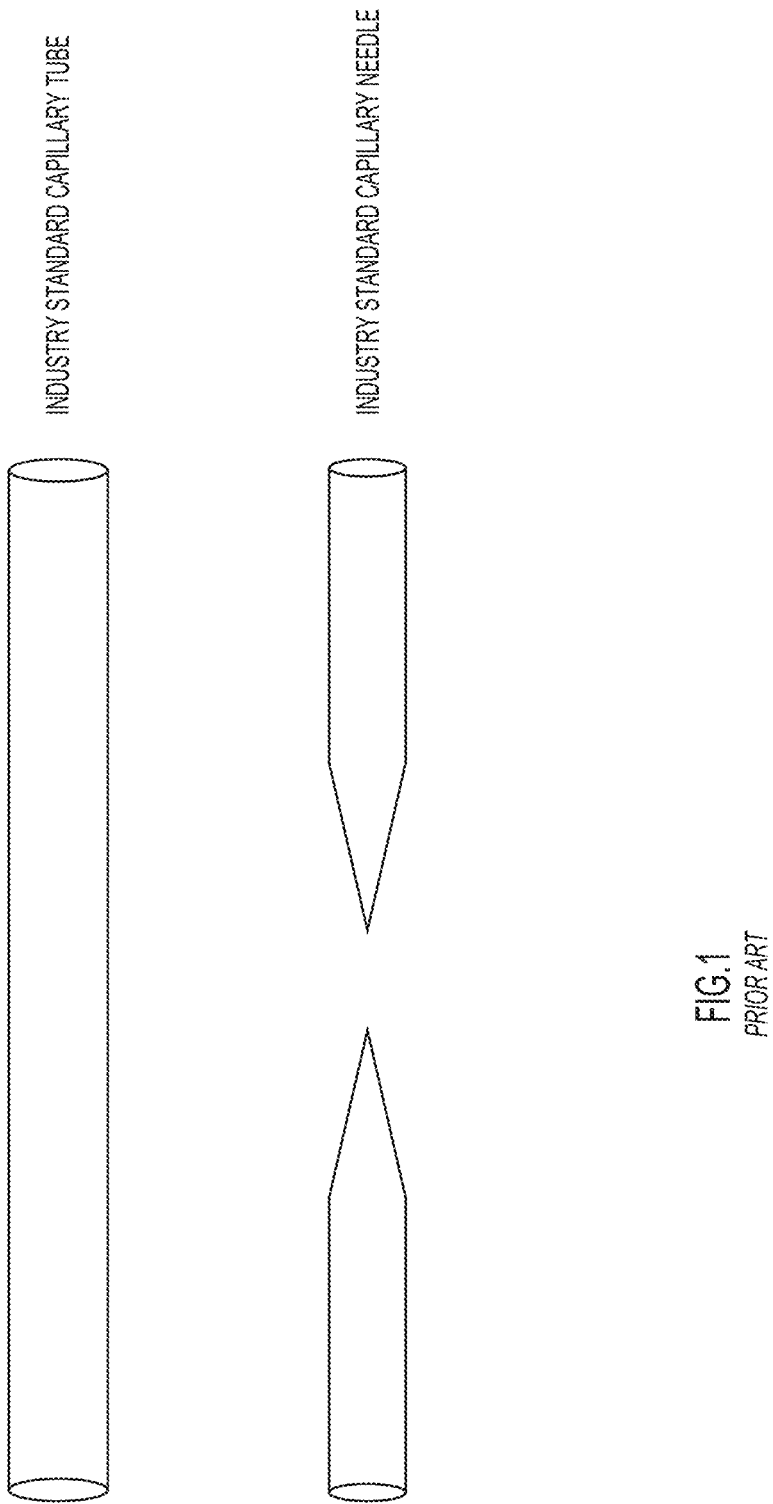
FIG. 1 is an illustration of a micro-capillary tube and needle, according to the prior art.
Figure 2C:
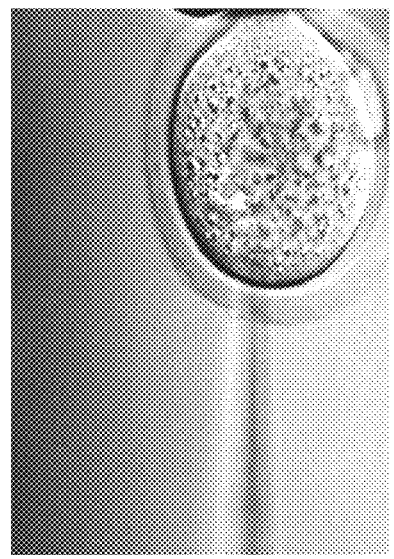
FIGS. 2A-2C show a prior art micro-capillary needle injecting a cell, in which the tip of the needle is difficult to visualize, according to the prior art.
Figure 2B:
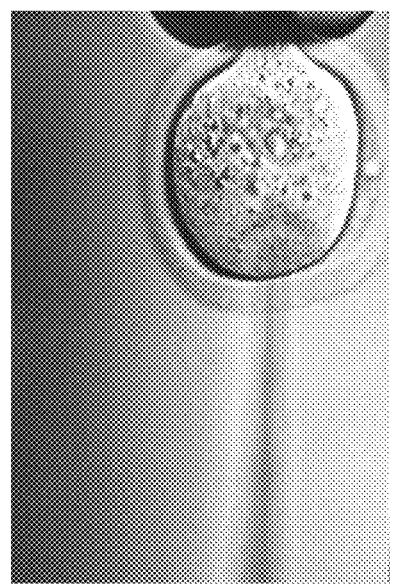
Figure 2A:
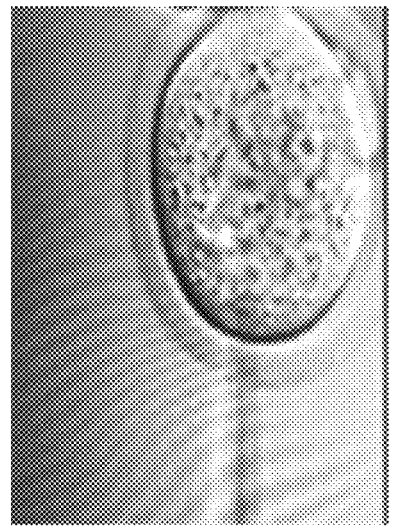
Figure 3:
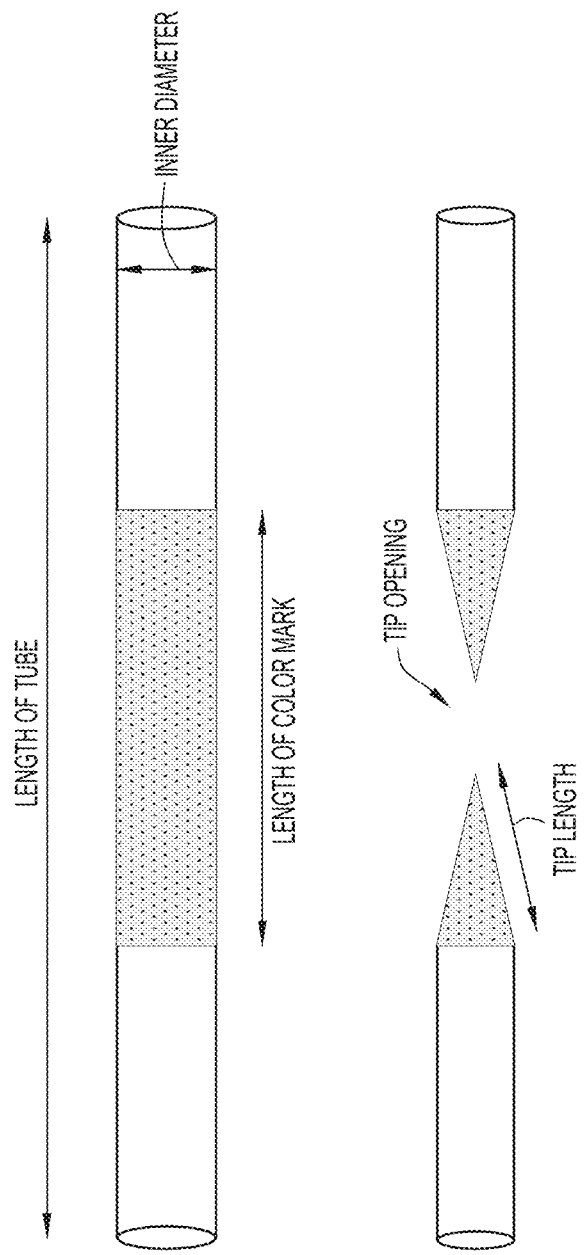
FIG. 3 is an illustration of a micro-capillary tube and needle, which have been coated with color marking reagent to visually enhance contrast with a biological material and with a non-adhesive reagent, according to aspects of the present invention.

FIG. 3 shows an illustration of a color marked capillary tube and a color marked microneedle/micropipette. In aspects, the biological material may be stained (e.g., using immunocytochemistry or other colorimetric techniques) and the tint/color may be selected to contrast the stained biological material.

Figure 4:
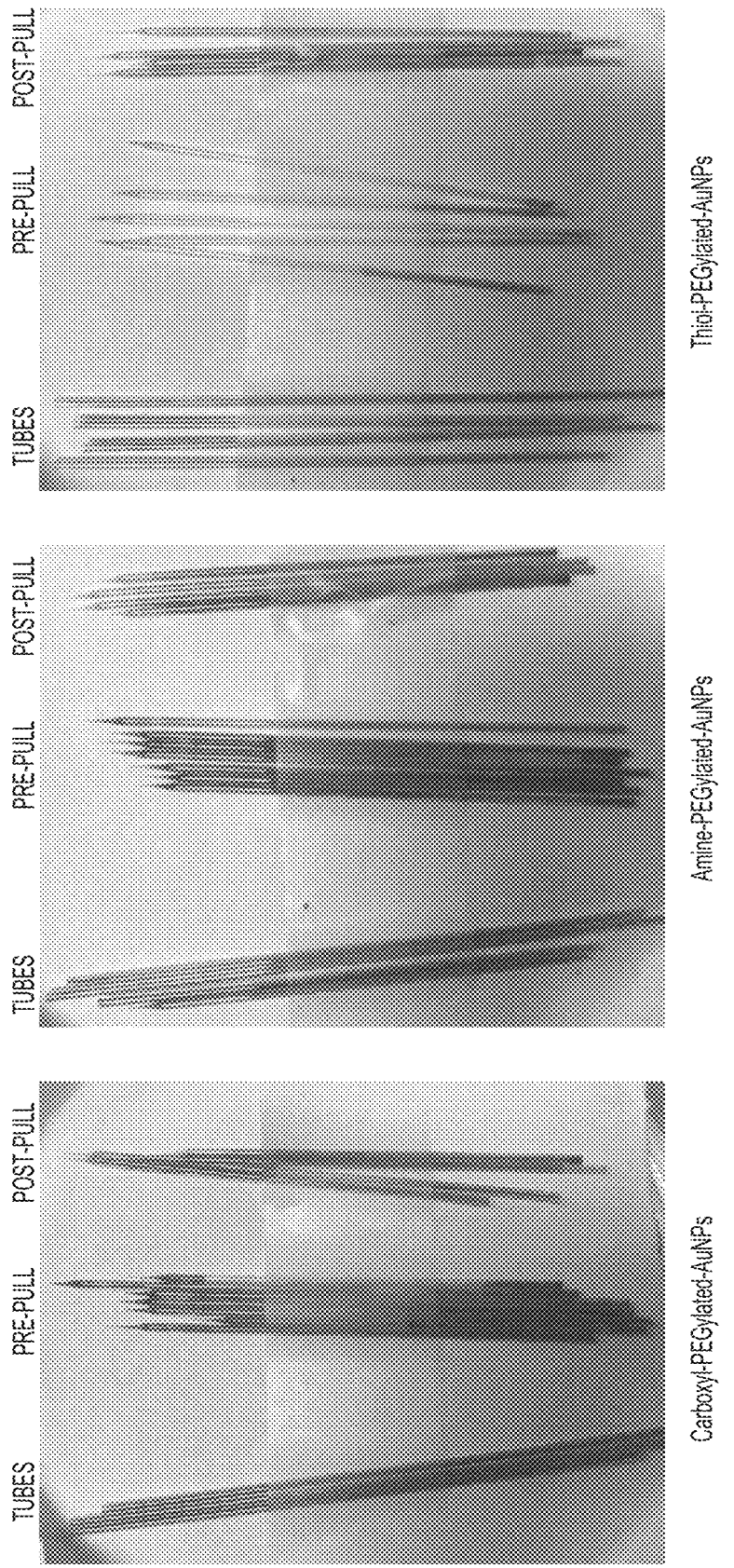
FIG. 4 shows various types of micro-capillary needles for injecting a cell in which the tip of the microneedle may be visualized intracellularly, according to aspects of present techniques.

FIG. 4 shows various microinjection needles with a color mark from gold nanoparticles. These needles may also have an anti-clogging and anti-adhesive coating. In the case of a glass microneedle, the anti-clogging reagent/anti-adhesive reagent may coat the exterior and the interior of the glass surface, respectfully, such that when the capillary tube is pulled using a micropipette puller and divided into two needles/pipettes, each needle has a color mark and anti-clogging/anti-adhesive reagents at or near its tip.

The color mark at the tip enhances microneedle visibility as the microneedle penetrates the biological target (e.g., a cell membrane). The color mark is generated by a color marking reagent which may be a heat resistant, non-cytotoxic, non-adhesive dye, nanoparticles, transition metals, or a fluorescence material that can be visualized under a fluorescence or non-fluorescence microscope. While injecting a material into a target cell type or tissue, the tip of the needle may be visualized under the microscope to provide more accurate and efficient microinjection techniques. Further, the user may target the microneedle much more accurately to a specific organelle, a domain within the cell, to gaps between cells, etc., to inject the material more precisely while reducing calibration variability.

For microneedles or micropipettes, at least the microneedle tip or micropipette tip is tinted. In some aspects, the length of the microneedle or micropipette that is tinted may range from 1 to 100%, from 1 to 50%, from 1 to 25% from 1 to 10% or from 1 to 5% of the length of microneedle or micropipette. For microtubes, at least a region (e.g., the middle region) of the microtube is tinted/colored, such that a pair of tinted microneedles or micropipettes may be generated from the tinted microtube. Similarly, the length of the microtube that is tinted may range from 1 to 100%, from 1 to 50%, from 1 to 25% from 1 to 10% or from 1 to 5% of the length of the microtube. In general, at least the tip of the microneedle or micropipette will be visible at locations proximal to cells, inside cells, between cells, in stained cells, in a whole tissue, in stained tissues, or with respect to an injectable substance, according to aspects of present techniques. In some cases, such as semi-transparent colorations, the marking may cover the entire length of the tube.

Figure 7A:
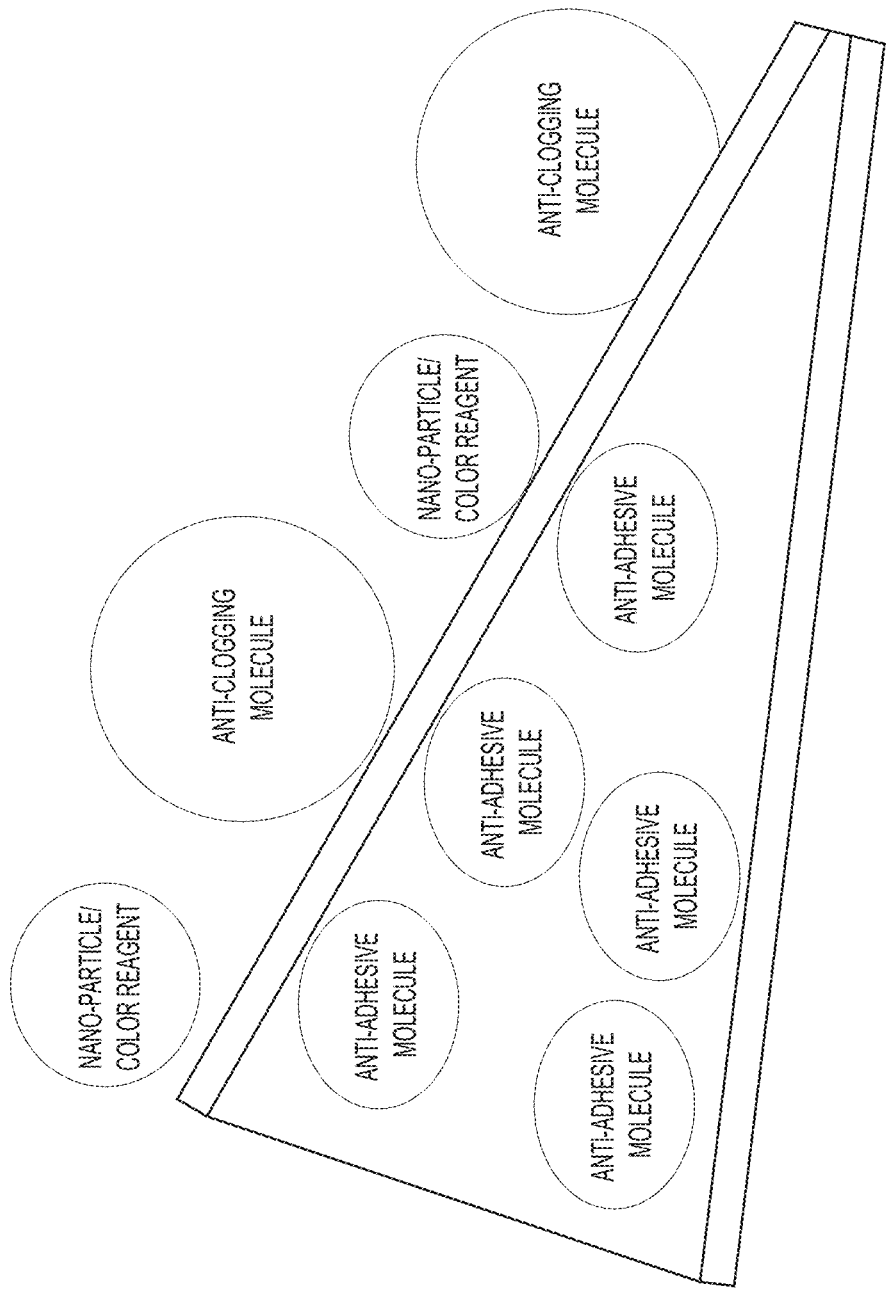
FIG. 7A is a schematic of a micro-capillary tip including a non-adhesive reagent/molecule bound to the interior of the tip and a color marking reagent and anti-clogging molecule that are independently bound to the exterior of the tip, according to aspects of the present invention.

With reference to FIG. 7A, a color marking reagent may be applied to the exterior glass surface of the micropipette, microtube, or microneedle. In some aspects, a non-adhesive/non-clogging reagent may also be applied to the exterior glass surface of the micropipette, microtube, or microneedle. In this example, both the color marking reagent and the non-adhesive/non-clogging reagent bind to the exterior glass surface independently of each other. The non-adhesive/non-clogging reagent binds to the interior glass surface. Thus, the exterior surface has attached to it both the color mark and the non-adhesive/non-clogging reagent, while the interior surface has attached to it the non-adhesive/non-clogging reagent.

In general, while the same reagent may be used for non-adhesion and non-clogging, the function of these two reagents may differ in that the non-clogging reagent serves to prevent or reduce cell adhesion and intracellular components to the exterior of the microneedle and reduce tip clogging, while the non-adhesive reagent serves to prevent or reduce adhesion of the reagent (which may include cells) that is being injected into the cell, to the interior of the microneedle. In aspects, the anti-adhesive molecule may be present both in interior of the tip and the interior of the capillary tube. The anti-clogging reagent may be present at the exterior of the tip region, and may optionally be present along the exterior of the capillary tube.

In some aspects, the tint/color mark may comprise color-labelling nanoparticles, and the surface of the nanoparticles may be chemically modified to minimize clogging/protein adsorption during experimental procedures. In other aspects, the color mark may comprise fluorescent molecules, and the surface of the fluorescent molecules may be chemically modified to minimize clogging/protein adsorption during experimental procedures. In other cases, the non-adhesive/anti-clogging reagent is linked to the color marking reagent via a crosslinker, and the crosslinked molecule binds to the exterior of the glass surface of the tip.

In some aspects, the microneedles or micropipettes are formed from capillary tubes. Once formed, the tint/color and non-adhesive coating are applied to the microneedles or micropipettes. In this case, the microneedles or micropipettes are tinted/colored and modified to be non-adhesive after generation by the micropipette puller.

In other aspects, tint/color and the non-adhesive coating are applied prior to micropipette/microneedle generation by the micropipette puller. In this case, the microtubes may be tinted/colored and chemically modified to minimize protein adsorption. A micropipette puller may be used to generate microneedles or micropipettes from capillary tubes.

Materials

In one aspect, the microneedle or micropipette is formed from glass, metal, plastic, or a polymeric material. Present invention embodiments are not limited to these materials, and the present techniques may be applied to any material suitable for generating a microneedle or micropipette.

Types of glass include but are not limited to borosilicate glass, with or without inner filaments, aluminosilicate glass, and quartz. Borosilicate is commonly used in applications including microinjection, patch clamp, micropipette aspiration, etc. Aluminosilicate glass may be preferred for microinjection in some cases, as it is more rigid than borosilicate glass and is capable of withstanding forces associated with microinjection. However, aluminosilicate glass is malleable at a higher temperature than borosilicate and workable over a narrower temperature range. Thus, micropipette or microneedle tips made from aluminosilicate often have a shape of a fine tip with a short taper. Quartz exhibits superior mechanical, electrical, and optical qualities properties as compared to other types of glasses, due to its purity, but may be more expensive. Any of the aforementioned types of glass are suitable for use with the techniques provided herein. Other types of glass include but are not limited to soda-lime glass, neutral glass, aluminum silicate glass, lead glass, UV-glass, X-ray glass, sealing glass, etc.

Other materials, such as metal, may also be used to form microtubes/microneedles. Metals include but are not limited to stainless steel, titanium alloy, copper, aluminum, chrome, shape memory alloy, nitinol, platinum, or nickel. In these embodiments, the metal may be anodized. In this case, suitable reagents for non-adhesion and color marking should be capable of or modified to be capable of binding to the surface of the metal tip.

Types of plastic include but are not limited to molded plastics and/or plastics generated from the following: High-Density Polyethylene (HDPE), Polyvinyl Chloride (PVC), Low-Density Polyethylene (LDPE), Polypropylene (PP), Polystyrene or Styrofoam (PS), and Miscellaneous plastics (including polycarbonate, polylactide, acrylic, acrylonitrile butadiene, styrene, fiberglass, and nylon).

Polymeric materials may also be used for additive manufacturing and to form tinted/color marked microneedles/micropipettes. Polymeric materials may include but are not limited to polyglycolic acid (PGA) or polycolic acid (PCA), polylactic acid or polylactide (PLA), acrylate, or any other type of material suitable for 3D fabrication or micro-printing techniques or additive manufacturing techniques. PLA is a biodegradable and bioactive thermoplastic aliphatic polyester that is often used in implantable medical devices due to having a high degree of biocompatibility with humans, as the degradation product, lactic acid, is metabolically innocuous. PGA is also a biodegradable, thermoplastic, linear, aliphatic polyester, which may be used to form the microneedles and micropipettes described herein, and is often used in biomedicine and tissue-engineering applications. Any material suitable for 3D printing applications, such as an acrylate group type material, may be used with the devices and techniques provide herein.

In some cases, 3D printing may be used to form microneedles, and once formed, the microneedles may be coated with a tint/color and a non-adhesive coating. In other embodiments, the tint/color may be mixed with the liquid polymer and incorporated into the printed microneedle during manufacturing. In other cases, the microneedle can be formed from different materials such that one of the materials is colored, such as in multi-material DLW, or other additive manufacturing technologies. In general, the materials are biocompatible.

Shape

Figure 5:
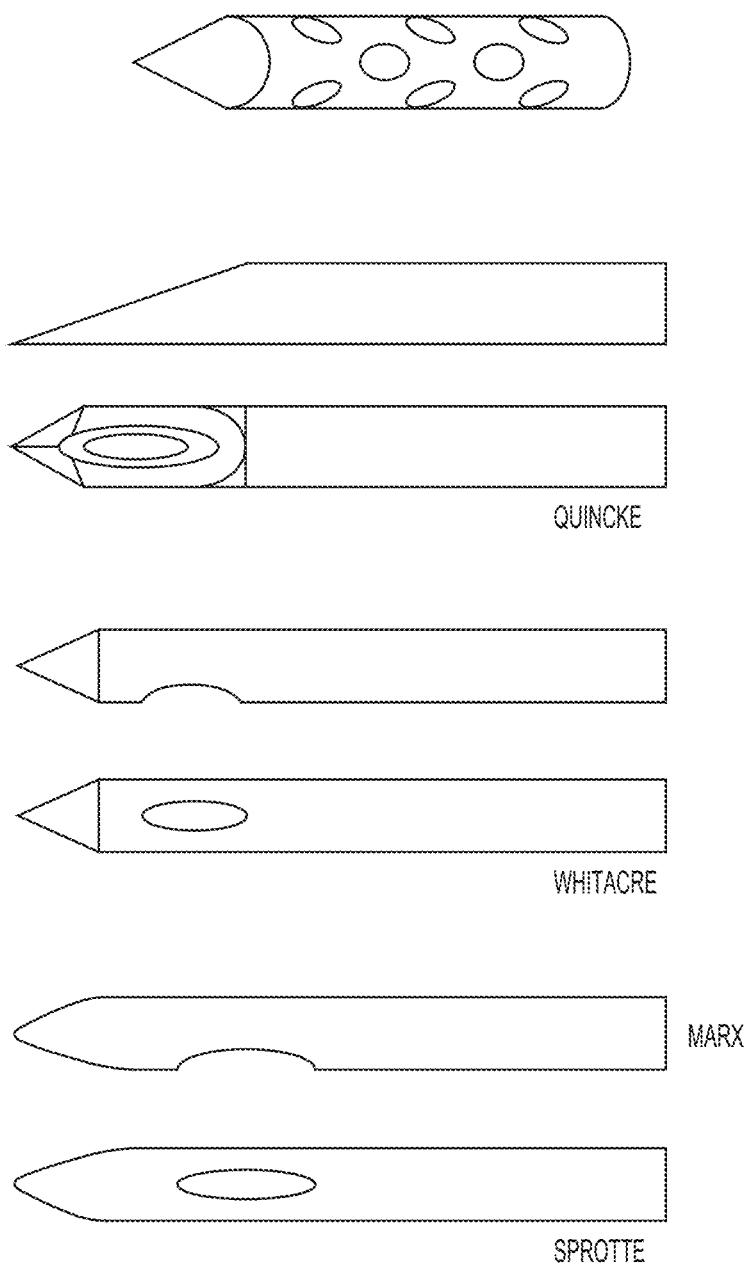
FIG. 5 is an illustration of different shapes of microneedles, according to aspects of the present invention.

In some aspects, the microneedles or micropipettes may include any suitable shape. For example, the tip of the microneedle/micropipette may be beveled, pointed, blunt, rounded, curved, or otherwise shaped. In some cases, openings may be present in the sides of the microneedle/micropipette tips. Example configurations include, but are not limited to, the shapes shown in FIG. 5. As shown, each of these shapes comprises a relatively long tubular or cylindrical region of substantially constant diameter and a shorter distally tapered tip region extending from the distal end of the of the tubular region.

The capillary tubes may include a variety of configurations, including but not limited to, a tube with a filament, a tube without a filament, a thin wall tube with a filament, a thin wall tube without a filament, a single barrel tube, or a multi-barrel tube (e.g., 2, 3, 5, 7 barrels, or other combinations), a piggyback tube, a septum theta, or any other suitable configuration and design for micro-capillary tubes.

In some aspects, the capillary tube has an outside diameter ranging from 0.5 mm to 2.00 mm prior to pulling with a pipette puller. The micropipettes and microneedles formed from the capillary tubes may have an inside diameter ranging from 0.2 µm to 1.56 mm, or any diameter in between, as customized based on the experimental application. In other aspects, holding pipettes to hold a cell in a position during microinjection may have an outer diameter between 65-180 µm and an inner diameter of 5-30 µm. Many shapes and sizes are possible, and all such shapes and sizes fall within the scope of the embodiments provided herein.

Figure 7B:
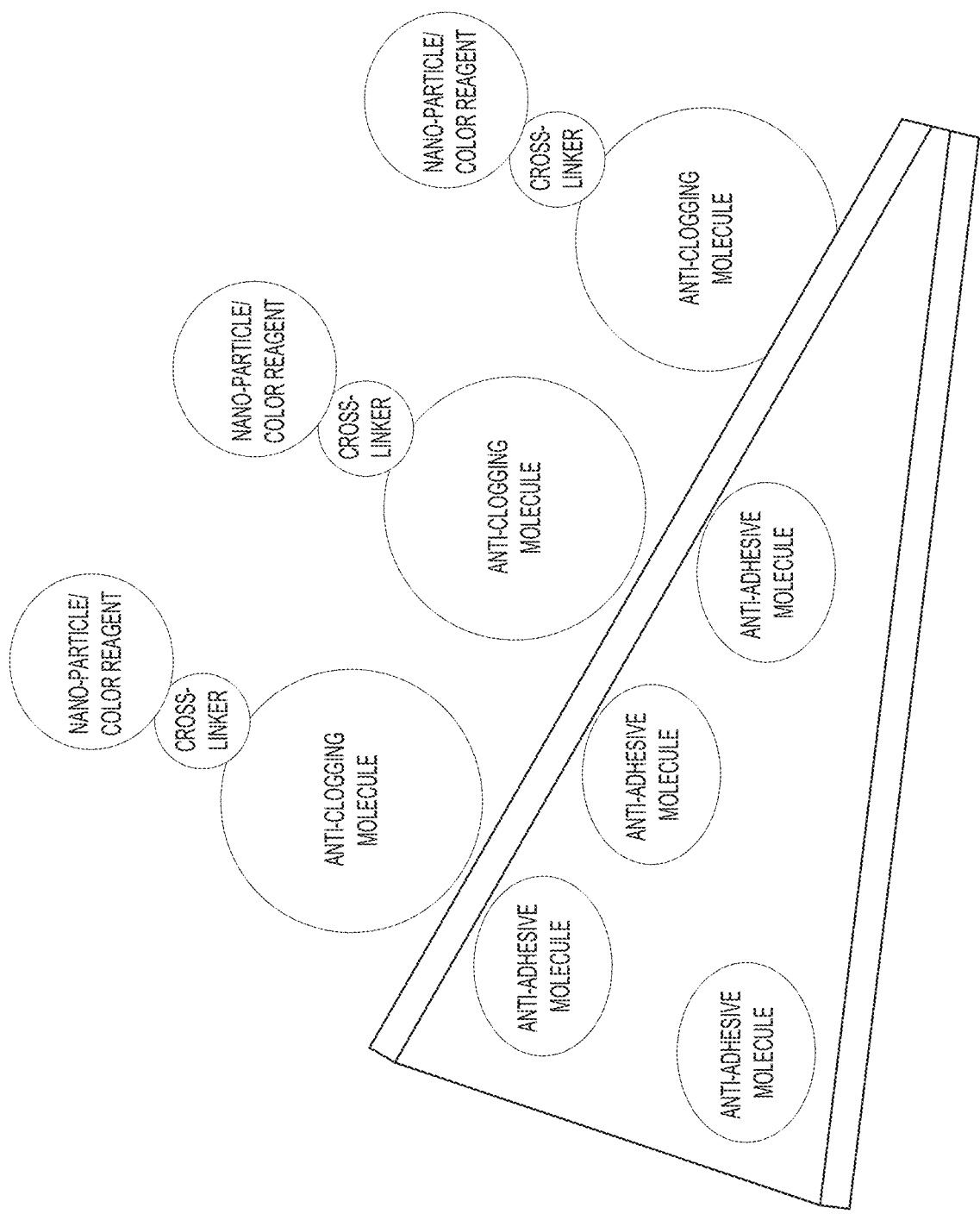
FIG. 7B is a schematic of a micro-capillary tip including a non-clogging reagent/molecule conjugated to a color marking reagent via a crosslinker bound to the exterior of the tip and an anti-adhesive reagent/molecule bound to the interior of the tip, according to aspects of the present invention.

In still other aspects, the dimensions of the microneedle may be sized based upon the material from which it is formed, the material to be injected or transferred through the microneedle or micropipette tip, and/or the material (e.g., cell, oocyte, tissue, etc.) into which the microneedle is inserted. Accordingly, the microneedle may be of any suitable length with any suitable diameter. Microneedle inner walls can include microstructures or anti-adhesive materials/coatings to prevent adhesion of a cell or other material being injected into an object to the inner walls of the microneedle, as shown in FIGS. 7A-7C. Microneedle outer walls can include anti-clogging materials/coatings to prevent clogging of the microneedle tip by cytoplasmic or other components during injection when the microneedle is inside the biological object.

Coatings

In another aspect, the tinted micro-capillary tube or microneedle is coated with a material that is resistant to adhesion of biological materials, thereby providing an anti-clogging and anti-adhesive capability. The anti-adhesive and anti-clogging reagent may be applied prior to micro-capillary needle preparation or applied after the microneedle is formed and ready to use.

Referring again to FIG. 4, the tinted microneedle provides greater visibility for the user during any application for which micro-capillary needles of any material may be used. In an example, a holding pipette may be present to position a cell. Using a tinted microneedle for injection, the user is able to more easily visualize the needle inside the cell, and is less likely to break the needle tip. This allows end-users to more easily use the microneedle/micropipette apparatus described herein. In addition, various substances can be introduced into cells more accurately and with high efficiency, without missing the target cell or organelles within the cell, and clogging and adhesion may be reduced using the reagents and techniques provided herein.

These materials are exemplary, and the present devices (e.g., tinted/non-clogging capillary tubes, tinted/non-adhesive microneedles, tinted/non-adhesive micropipettes, etc.) are not limited to these particular materials. In general, anti-clogging materials coat the outside of the capillary tube, micropipette or microneedle to prevent the cytoplasmic materials inside of the object to clog the needle tip during and after penetration. Anti-adhesive materials coat the inside of the microneedle to prevent a cell or other material that is being injected into the object from adhering to the inner walls of the micropipette or microneedle. In some cases, the same material may be used for anti-clogging and anti-adhesion; in other cases, the materials may be different.

In general, materials for anti-adhesive and anti-clogging coatings will be non-toxic and compatible with cells and tissues.

Tinted/Color Marked Microneedles/Micropipettes

In an embodiment, color marked microneedles or micropipettes may be generated using gold nanoparticles (AuNPs) or gold-silver alloy nanoparticles (AuAgNPs) to produce a broad range of colors. In some aspects, the microneedle or micropipette may be coated with a suspension of gold or gold-silver alloy nanoparticles. In some aspects, colloidal gold nanoparticles may be used. In general, the optical and electronic properties of gold or silver nanoparticles are tunable by changing the size, shape, surface chemistry, or aggregation state of the nanoparticles. In some aspects, the color of the nanoparticles is related to particle size. As the particle size increases for gold nanoparticles, the color may shift from a vibrant red, to pink, and then to purple.

Any color of nanoparticle may be used, provided that the nanoparticles are heat resistant (if exposed to pipette pullers), stable after attachment to the microneedle/microtube, non-cytotoxic, and preferably approved by a regulatory agency for human use.

In other aspects, glass may be doped with reagents, including but not limited to transition elements including $Fe_2O_3$, $Cr_2O_3$, and $CoO$ that provide color to the glass itself. After doping, the glass may be silanized to render the doped glass inert. The glass surface may then be PEGylated or coated with other anti-clogging and anti-adhesive material (s) such as copolymers.

In still other aspects, suitable anti-adhesive or anti-clogging reagents may include: copolymers containing poly sulfobetaine methacrylate (polySBMA); copolymers containing poly carboxybetaine methacrylate (polyCBMA); and polymers containing poly(2-methacryloyloxyethyl phosphorylcholine) (polyMPC). Any suitable polymer may be used, provided that the polymer prevents or reduces binding of biological material to a glass surface.

In some aspects, distinctive color marks may be provided in or on the microneedle, which may be achieved by using a color marked microtube/microneedle or by marking a transparent tube with color marked sections such as stripes, dots, etc., in addition to the coating comprising the anti-clogging agent and/or anti-adhesive agent. Irradiating the glass capillary can also create color marks. Alternatively, the surface of the microneedle tip may be texturally treated to render it optically reflective or more refractive to enhance its visibility in situ.

AuNPs and PEG may be attached to the surface of a microneedle using the following protocol. In the case of glass micropipettes, glass may be cleaned and sonicated with a combination of soap, water, ethanol, and acetone. The dried glass may be immersed in Piranha solution, comprising $H_2SO_4$ and $H_2O_2$, and then washed thoroughly with deionized water. Glass may be incubated for silanization in APTES ((3-Aminopropyl) triethoxysilane)) and then incubated with functionalized PEG-AuNPs through an EDC-coupling reaction. AuNP is ideal for staining substrates because it is inert, heat resistant, non-cytotoxic and approved for human use.

A variety of options exist for attaching PEG to a surface such as silica or glass. For example, PEG-silane reacts with hydroxylated surfaces such as silica and glass. PEG-thiol reacts with noble metal surfaces such as gold, silver, etc.

Different PEGylated nanoparticles may be generated, for example, including carboxyl-PEGylated-AuNPs, amine-PEGylated-AuNPs, and thiol-PEGylated-AuNPs. EDC coupling may create a network of amines and carboxyls to increase coloration and to attach PEG molecules to the glass. Example structures are provided as follows:

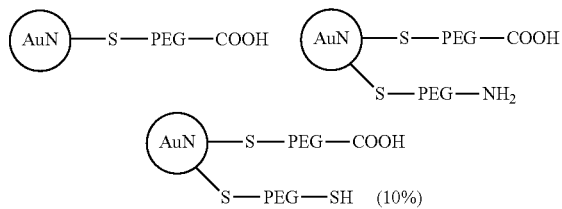

A wide range of molecules in addition to nanoparticles are suitable as color marking reagents, and all such molecules are contemplated for use herein. Other options include changing the glass reflecting index, and fusing inorganic materials into the glass.

Referring to FIG. 7A, a glass capillary may be coated with an anti-adhesive reagent and a color marking reagent. In some aspects, the color marking reagent may be applied first, followed by the anti-adhesive reagent. In other aspects, the anti-adhesive reagent may be applied first and the color marking reagent may be applied second. In this example, both types of molecules/components may bind independently to the glass surface. With respect to the microneedle/micropipette, it is understood that the anti-adhesive molecule may be present both in the interior of the tip and the interior of the capillary tube. The anti-clogging reagent may be present at the exterior of the tip region, and may optionally be present along the exterior of the capillary tube.

Referring to FIG. 7B, an anti-clogging agent may be crosslinked to a color reagent. In some aspects, the anti-clogging agent is PEG or any suitable polymer or copolymer. In some aspects, the cross-linker is any cross-linker capable of connecting a nanoparticle capable of producing a color mark to an anti-adhesive/anti-clogging agent. In some aspects, the nanoparticle may be Au or Ag nanoparticles or a combination thereof, and the crosslinker may be 1,2-ethanedithiol (EDT). With respect to the microneedle/micropipette, it is understood that the anti-adhesive molecule may be present both in the interior of the tip and the interior of the capillary tube. The anti-clogging reagent may be present at the exterior of the tip region, and may optionally be present along the exterior of the capillary tube.

FIG. 7C shows an example micropipette or microneedle comprising microstructures in the interior of the micropipette. In this example, microstructures are present in the tube portion while the color marking reagent is present at the tip.

It is noted that the tip may also contain an anti-clogging reagent, at the exterior of the tip and an anti-adhesive agent at the interior of the tip. In some aspects, a molecule capable of inducing a behavior in a biological tissue or cell may be attached to the exterior of the tip, for example, molecules that induce motility, growth, or cell division may be provided. In some aspects, the microstructures may be printed by 3D/additive manufacturing. In aspects, the microstructures may have the shape of thin filaments, or other structures with reduced surface area to reduce the area to which a cell or biological material may adhere.

Production Techniques for Different Needles

Microinjection needles may be generated with either a horizontal or vertical pipette puller. The capillary tube is secured into the pulling apparatus so that the heating element is approximately at the center of the capillary tube and the temperature and pulling force are programmed to generate a microneedle with a specified tip shape and/or taper. One capillary tube typically produces two usable needles.

Once produced, the microneedle, for instance, having a tip size of about 1-5 μm or other size is filled with the substance to be introduced into the target. The substance is forced from the capillary by hydrostatic pressure (pressure injection) or by an electric current (iontophoresis) or by any other suitable technique, into the cell or tissue.

In other aspects, the microneedles may be formed using any suitable 3D printing technology/additive manufacturing techniques, including but not limited to, stereolithography (SLA), Fused Deposition Modeling (FDM), Direct Laser Writing (DLW), Passive Self-Peeling (PSP), and Digital Light Processing (DLP), etc. In general, these techniques are suitable for preparing microneedles that are made of materials other than glass, such as different types of silica. For example, silica may be used for additive manufacturing (3D fabrication).

Additive manufacturing or "three-dimensional (3D) printing" may be used to produce devices at a submicron scale, including the microneedles and micropipettes provided herein. DLW uses tightly focused femtosecond laser pulses to initiate spatially controlled polymerization (i.e., solidification) of a liquid-phase photoreactive material via two-photon (or multi-photon) absorption phenomena. By precisely positioning the focal point of the laser with a point-by-point, layer-by-layer manner, 3D structures comprising cured photomaterial can be additively manufactured with feature resolutions on the order of 100 nm. In some aspects, galvanometric scanning micromirrors may be used to rapidly produce functional commercial products. Upon completion of the DLW process, a development protocol including successive rinses in propylene glycol monomethyl ether acetate (PGMEA) and 50% 1-propanol, 50% 2-propanol can be utilized to remove any remaining uncured photomaterial.

Microneedle and micropipette architectures may be designed by using computer-aided design (CAD) software and then converting the models to the widely used stereolithography (STL) file format. The STL file may be imported into computer-aided manufacturing (CAM) software to convert the solid model into a point-by-point, layer-by-layer laser writing path. This writing path is calculated based on three fundamental parameters: (i) contouring (number and spacing), (ii) hatching (spacing, angle, and angle offset), and (iii) layer height. For each horizontal layer, the contours (alternatively referred to as "shells") are defined by the outer bounds of the structure and refer to the number of times that the laser traces this geometry (starting from the outer walls and working inwards). The hatching (or "infill") settings determine the route by which the laser will fill the remaining internal space (i.e., within the contours). Lastly, the layer height sets the thickness of each horizontal layer, and thus, the vertical resolution of the printed structures.

Submicron-scale additive manufacturing technologies offer the potential to revolutionize microinjection efficacy via substantive versatility in the design and fabrication of the microneedle tip, while also providing a new set of capabilities for other areas that require high-performance, customizable microneedles. In some aspects, DLW or other suitable printing techniques may be used to manufacture microneedles based on entirely new architectural designs that are functionally advantageous, yet unfeasible to fabricate via conventional methods. The advantages of the 3D needle, include but are not limited to: (1) repositioning the singular needle opening from the "top" of the tip to the "sides" (e.g., singular or multiple "side-port" openings with a sealed, yet fine-point tip) to substantially reduce needle clogging as cytoplasmic material will have to block multiple openings in order to obstruct the side-port(s) (see also, FIG. 5). (2) the submicron-scale precision of DLW will yield high needle-to-needle print repeatability, thereby eliminating or minimizing multitudinous calibration processes, (3) multimaterial DLW of microneedles with selectively patterned visible contrast coloring will augment visual tracking within the target; and (4) better mechanical performance and stronger needle structure will allow use of the needle in mechanically rigid objects or objects resistant to microinjection.

Thus, 3D printing offers a variety of advantages. With 3D printing, the tip shape can be controlled and customized, allowing openings to be placed nearly anywhere along the length of the tip as well as reproducibility with regard to generating openings of a particular size and controlled tapering. Additionally, the mechanical rigidity of the microneedle may be customized to the application by selection of particular materials to print the microneedle or particular geometries of the microneedle. Applications that may need tips of higher rigidity can be created by changing the material or geometry (e.g., shape or taper of the tip). In some aspects, hybrid microneedles may be formed from different types of materials, e.g., to generate transparent regions and non-transparent regions or regions with differing rigidities. In other aspects, 3D printing techniques may be used to create color mark patterns on a micropipette or microneedle to enhance visibility. In one application, 3D printing may be used to mark a micropipette or microneedle with corresponding graduation marks for volume and/or length.

Reagents for Anti-Clogging, and Anti-Adhesive Properties Microneedle and Micropipettes Clogging of microneedles or micropipettes during microinjections or other experiments, particularly over time, due to protein and lipid adsorption, can greatly affect experimental rigor and reproducibility. To minimize clogging, the surface of the color marked microcapillary needle may be coated with hydrophilic substances (e.g., PEG), including but not limited to polyethylene glycol (PEG) passivating ligands and other copolymers, including polySBMA, polyCBMA, and polyMPC. MPC (Methacryloyloxyethyl Phosphorylcholine), polySBMA, polyCBMA are neutral molecules with protein-like properties that inhibit proteins from adhering to coated surfaces.

PEG-based coatings may be used to minimize non-specific binding of macromolecules to surfaces. In some aspects, the binding affinity of macromolecules (e.g., proteins, lipids, etc.) to a surface is governed by electrostatic interactions and hydrophobic interactions. To enhance anti-clogging capabilities of the microneedle, PEG or similar ligands that terminate with a thiol or amino/amine group on one end to facilitate binding to the nanoparticles and a carboxyl group on the other end to render the microneedle/microtube negatively charged may be used.

In some aspects, micropipettes or microneedles fabricated by 3D printing technology may not need an anti-clogging/anti-adhesive coating, as the mechanical structure (e.g., one or more side openings, microstructures, etc.) may limit clogging from biological materials. In some aspects, the microstructures cover or coat the interior walls of the microneedle/micropipette to prevent cells that are being injected from adhering to the interior surface of the microneedle.

In other aspects, for the 3D fabrication process, PEG or other non-adhesive materials may be added to the interior walls of the microneedle to prevent adhesion, such as from sperm adhering to the interior wall of the microneedle during injection into a cell from Intra Cytoplasmic Sperm Injection (ICSI) as part of Artificial Reproductive Techniques (ART) procedures.

Microneedles may be produced by programming pipette pullers to pull borosilicate glass capillaries (e.g., 1.0 mm OD, 0.75 mm ID) or any other variety of glass capillaries to produce a tapered needle. In some aspects, needles taper quickly (within ~5-7 mm) to a sharp but open point (e.g., having an inner tip diameter of 1 um or greater). Shapes and color markings may be customized by the user. For example, a user may design a particular program by a micropipette puller to produce a micropipette or microneedle having a specified taper and inner tip diameter. In other cases, a user may select a particular nanoparticle in a particular ratio to produce a desired color in order to provide contrast to a biological sample (e.g., unstained sample, stained sample using a particular reagent or combination of reagents). For needle pullers that produce a closed tip, the tip may be opened by gently tapping the needle across a glass slide, or by moving the needle against debris on an agarose pad under a microscope or by another manual method developed in the lab (e.g., forceps, razors, etching, etc.) to break the glass. Injection pads or molds may be used to organize and orient the injected cells. Needle-loading pipettes may be used to upload the material to be injected into the cell into the interior of the microneedle/micropipette.

Advantages

Present devices and techniques offer a new and substantive improvement from transparent microneedles. Present high contrast, anti-clogging and anti-adhesive microneedles offer customizable high-contrast color, are resistant to clogging and adhesion, provide an unparalleled level of geometric control with feature resolutions on the order of 100 nm, and enable extensive flexibility in designing the microneedle tip.

The devices and techniques presented herein are compatible with a wide range of micropipette and microinjection techniques, and may be implemented in a variety of experimental systems and protocols, examples of which are provided below. These devices and techniques improve the rigor and reproducibility of microinjection and other experiments, and may be applied to a variety of cell types in many organisms for applications in basic science research, in various medical applications and related research, for biopharmaceutical companies, and in stem cell research/gene therapy applications. Examples include but are not limited to stem-cell gene manipulation, intra-cytoplasmic sperm injection (ICSI), and human disease prevention modeling via pathophysiological investigations.

A variety of features of the high contrast and/or anti-clogging and anti-adhesion microneedles, microtubes, and micropipettes distinguish the present microneedles from existing microneedles. According to present techniques, the color mark is localized to the tip of the microneedle/micropipette or at the center of a glass capillary tube prior to becoming a microneedle/micropipette. The color mark increases the contrast visibility of the tip of the needle inside and outside the biological target (e.g., cells and tissues). Additionally, the color of the needle may be customized by selecting suitable color reagents to achieve a desired contrast for a desired application. For example, a different color mark may be selected for cells that have been stained with a particular reagent versus cells that have not been stained or have been stained with other reagents. Using this technology, the color marked tip may be visualized outside and inside the biological object, allowing injected material to be delivered into a specific location within the cell during microinjection.

Present techniques are compatible with a wide variety of microinjection applications. Visualization of the color of the needle tip may be performed under ambient/visible light, or in other cases, using fluorescence light.

Present devices are suitable for use with precision positioning devices, e.g., a micro-manipulator to position microneedles or micropipettes. The microneedle inner diameter opening may be in the range of about 0.2-10 microns or more and the outer diameter is in the range of 1-3 mm. These dimensions provide for microinjection of nanoliters (nL) of a substance into a specific location of a biological target. In addition, the needle may be formed from glass or any suitable 3D printing technology and from a variety of materials/resins.

EXAMPLES

The following section includes example protocols and/or applications that may utilize the microneedle and/or micropipettes described herein. These examples are intended to be non-limiting, as the tinted anti-clogging and anti-adhesion microneedles may be used with any application involving microneedles or micropipettes and is fully customizable per specific requirements of the experimental biological system.

Example 1. Microinjection

Microinjection, a mechanical process, uses a micropipette to inject a substance at a microscopic or near microscopic level. The target is often a living cell but may also include other targets such as intracellular space or tissue. Microinjection is usually performed by viewing a target with an inverted microscope having a magnification power of around 200×, though it may also be performed using a dissecting stereo microscope at 40-50×, or a traditional compound upright microscope at similar power to an inverted model.

For cellular or pronuclear injection, the target cell is positioned under the microscope and two micromanipulators, one micromanipulator holding a holding pipette (or other holding device) and the other micromanipulator holding the microneedle (usually between 0.5 and 5 μm in inner diameter but may be larger if injecting stem cells into an embryo), moves the microneedle toward the cell, thereby applying force to penetrate the cell membrane and/or the nuclear envelope. This technique may also be used to introduce a vector/plasmid into a single cell. Microinjection may be used in a variety of experimental techniques, including the cloning of organisms, genetically modifying organisms, and treating male infertility through intracytoplasmic sperm injection (ICSI). Holding pipettes are typically blunt flame-polished pipettes through which suction is applied to immobilize the biological target (e.g., a cell, a blastocyte, etc.).

Example Microinjection Method:

An example microinjection protocol may include the following steps:

Fill a microneedle-loading pipette by capillary action with the material to be injected.

Insert the loaded pipette into the large diameter end of the injection needle and expel the injection material into the microneedle. Confirm that the injection material is drawn into the microneedle tip. Multiple injection needles can be prepared and stored by resting the filled microneedles across raised clay or wax ridges within a covered humid box.

Place a loaded needle into a needle holder mounted on the micromanipulator. After this step, the tip of the microneedle may be opened manually to the desired size based on the microinjection application and/or injected target. For example, the tip of the microneedle may be opened/calibrated to a desired size by using a razor/forceps to snip off the tip, creating a beveled opening.

Calibrate the microneedle by injecting one drop of the material onto parafilm or another surface to measure droplet size. Estimate the concentration of the injected material based on drop size.

Align the cells or embryos (or other biological target) for injection on the injection mold or pad.

Position the microneedle so that the tip is in the center of and proximal to the target.

Apply pressure to test if there is a flow of injected material. If not, the needle may be clogged. In this case, clear the obstruction with a pulse of high pressure (without exceeding the pressure tolerance of the system, which will cause needle ejection and possibly gasket damage). If this fails, other techniques may be performed including contacting the needle tip comprising debris with the pad surface and moving the microneedle tip to drag the needle on the surface of the pad to clean the tip. This approach induces flow without breaking the micropipette tip. Alternatively, the tip may be broken by gently contacting a particle embedded within the pad while under pressure. Otherwise, a new needle may be needed, and the fill and calibration process repeated.

Insert the microneedle into a target (cell, tissue, embryo, etc.) such that the tip is inside the cell. Using the micromanipulator, move the needle tip into the same focal plane, directly adjacent to the targeted location. Using fine X-axis control, position the microneedle tip into the center of the cytoplasmic core. Inject the material by applying pressure so that solution flows freely and smoothly into the cell. Once injection is completed, the tip of the microneedle may be removed from the object.

Recover the cells/embryos by collecting all injected cells/embryos and returning them to the incubator for further growth and development.

In some aspects, microinjection is performed using a vibration table, which is a heavy table segregated from strong vibrations and air currents.

A pressurized injection system (oil base or a gas base) may be used to provide force for material injection, and may be accompanied by a microneedle holder. The microinjection needle may be placed in the microneedle holder with a tight-seal collar, which may be attached by plastic tubing to a regulated pressure source of the injection system. In some cases, the pressure regulator may be attached to a nitrogen gas tank.

The color marked tip can also be an inducible pipette by fusing different components/materials to the tip of the microneedle. This pipette, once inserted into the biological target, can then trigger/induce a secondary biological process.

Example 2. Transgenic Animals

The devices and techniques provided herein are compatible for use with microinjection techniques to generate transgenic animals, which may be used as models for biological and medical research and therapeutic-based applications. For example, microinjection may be used to insert a foreign gene into an animal cell or other biological target. In some cases, the injected material becomes integrated into the host genome.

In some aspects, microinjection may be used to inject DNA into the pronuclei of a fertilized egg, which is subsequently implanted into the oviduct of a pseudopregnant surrogate mother. The transgenic host organism carries in all of its cells, a foreign gene, inserted by laboratory techniques such as microinjection, using a tinted non-adhesive microneedle.

Transgenic animals may be produced by at least three methods: microinjection of cloned gene(s) into the pronucleus of a fertilized ovum, injection of embryonic stem cells into embryos, or exposure to retroviruses (not discussed in detail herein). With microinjection, the foreign DNA is injected into the embryo's pronucleus with a finely drawn tinted microneedle covered in a non-adhesive coating. The second method involves microinjection of embryonic stem (ES) cells, which may be altered genetically, by microinjection of DNA using a tinted microneedle covered in a non-adhesive coating before production of embryos. These techniques are well known to a person of ordinary skill in the art.

Present techniques may be used with any suitable biological target including cells from mouse, cows, rabbits, chicken, goat, hamsters, fish, pigs, sheep, *drosophila*, worms, donkey, horses, frogs, zebra fish, nematodes, rats, etc.

Microinjection may be used for a variety of applications, including but not limited to, visualization of vascular architecture, monitoring of movement and accumulation of injected substances (e.g., RNA localization) in the oocyte, and to understand developmental processes.

Example 3. Transgenic Plants

Present techniques and devices may be used to generate transgenic plants. Transgenic plants are plants that have been genetically engineered using recombinant DNA technology to create modified plants with new characteristics.

Present devices and techniques using the tinted, non-adhesive coated microneedles provided herein are compatible with microinjecting plant DNA or other biological material into target plant cells. These techniques have a variety of applications including injecting genes conferring resistance to certain insects and viruses or injecting genes conferring tolerance to broad-spectrum herbicides. For example, present techniques and devices may be used to introduce a gene into a tomato that delays over-ripening and prolongs the shelf life of the fruit.

Example 4. Somatic and Embryonic Stem Cell Gene Therapy

Somatic and embryonic stem cell gene therapy is directed towards the treatment/cure of genetic diseases in children and adults. In general, glass needle-mediated microinjection may be used to successfully deliver corrective DNA directly to somatic and embryonic stem cells as gene therapy. By utilizing innovative gene repair and compensation strategies, treatment of diseases, such as sickle cell disease, thalassemia, cancer and AIDS, may be targeted. Microinjection-based gene modification is also being applied to other somatic stem cell types, and may have applications in the fields of functional genomics, target gene validation, and transgenics. By obtaining pure or substantially pure populations of hematopoietic stem cells, nuclear microinjection methods may be used for transferring DNA. This technique combined with new highly sensitive methods for detecting cells with the specified genetic modification of non-expressed genes may accelerate the development of techniques that use homologous recombination-mediated gene therapy, for example, in hematopoietic stem cells. Human pluripotent stem cells can produce cell types needed for retinal regeneration, including embryonic stem cells (ESCs) and induced pluripotent stem cells (iPSCs). Both are defined by an unlimited ability for self-renewal and by the capacity to differentiate into a desirable adult cell type.

Example 5. Assisted Reproductive Technology (ART)

Present devices and techniques are compatible with techniques involving ART. For example, these techniques may include microinsemination, intracytoplasmic sperm injection (ICSI), preimplantation genetic diagnosis (PGD), and preimplantation genetic correction (PGC). With ICSI, a single spermatozoon may be selected and aspirated using a holding pipette. A tinted, non-adhesive microneedle based on the techniques provided herein may be used to inject biological material into the cytoplasm of the oocyte. Using PGC, genetic defects within embryos may be identified.

Example 6. Gene Targeting

Microneedles may be used to introduce a designed mutation into a germ line of an animal/plant by means of targeted modification of the ES (Embryonic Stem) cell genome. An ES cell, in which its genome is altered by a mutation, is injected into a blastocoel cavity of a preimplantation animal embryo and the blastocyst is surgically transferred into the uterus of a foster mother where development progresses to term. The resulting animal is chimeric in that it is composed of cells derived from both the donor stem cells and the host blastocyst. Gene targeting techniques, including microinjection, have a major impact on all phases of mammalian biology, including development, cancer, immunology, neurobiology, and human medicine.

Example 7. Eye Research and Brain Research

Present devices and techniques are compatible with techniques involving microinjection of the eye retinal pigment epithelium (RPE) and intraocular (IO) injection. Present devices and techniques are also compatible with techniques involving microinjection of different substances into brain structures and/or cells, including but not limited to manipulation and tracking of neural stems and progenitor cells in tissue at single-cell resolution.

Example 8. Tissue Engineering of Organs and Tissue

Present techniques may be used in the development of laboratory-grown tissues, referred to as organoids, bio-artificial tissue, or tissue-engineered constructs. Also, present techniques may be used to obtain transgenic organs from animals for clinical transplantation.

A goal of tissue engineering is to assemble functional constructs that restore, maintain, or improve damaged tissues or whole organs. Artificial skin and cartilage are examples of engineered tissues that have been approved by the FDA. However, the growing shortage of available organs is a major problem in transplantology. Thus, new and alternative sources of organs need to be developed. One promising solution may involve xenotransplantation, i.e., the use of animal cells, tissues and organs. For example, the domestic pig is the optimum donor for such transplants. However, xenogeneic transplantation from pigs to humans involves high immune incompatibility and a complex rejection process. The rapid development of genetic engineering techniques enables genome modifications in pigs that reduce the cross-species immune barrier.

Example 9. Therapeutic Cloning or Somatic Cell Nuclear Transfer (SCNT)

Present techniques are also compatible with therapeutic cloning. "Clonote" is a laboratory strategy for creating a viable embryo from a body cell and an egg cell. The technique consists of taking an enucleated oocyte and implanting a donor nucleus from a somatic cell, and may be applicable in both therapeutic and reproductive cloning.

Using a process of "somatic cell nuclear transfer," the cellular nucleus, which contains the genetic material, is removed from a somatic cell and transferred by injection into an unfertilized egg from which the nucleus has also been removed. Microneedles developed herein may be used to extract DNA material from the nucleus of a somatic donor cell and transfer it into a hollow egg. Therapeutic cloning may allow an individual's own cells to be used to treat or cure an individual person's disease, without risk of introducing foreign cells that may be rejected.

Example 10. Capillary Nano-Immuno Assay (CNIA)

In other aspects, microneedles and micropipettes may be used to offer precise and accurate measurement of proteins and their post-translational modifications using either charge-based or size-based separation formats.

Example 11. Regenerative Medicine

Regenerative medicine is a branch of translational research in tissue engineering and molecular biology which involves replacing, engineering, or regenerating human cells, tissues, or organs to restore or establish normal function. Regenerative medicine may generate living, functional tissues to repair or replace tissues or organs in which function is lost due to age, disease, damage, or congenital defects. One of the ultimate goals of regenerative medicine is the generation of patient-specific organs from pluripotent stem cells (PSCs). In some aspects, human organs may be produced using blastocyst complementation.

Example 12. Patch Clamp and Electric Potential Techniques

Patch clamp is a laboratory technique in electrophysiology used to study ionic currents in individual isolated living cells, tissue sections, or patches of cell membrane. This technique is especially useful in the study of excitable cells such as neurons, cardiomyocytes, muscle fibers, and pancreatic beta cells, and can also be applied to the study of bacterial ion channels in specially prepared giant spheroplasts. This technique uses micropipettes to record electrical activity in cells and for injecting a variety of substances for experimental purposes.

In other aspects, glass micropipette electrodes may be used to stimulate individual cells electrically and to study electrical potential in cells.

Example 13. Intracellular Recording

In other aspects, the micropipettes provided herein may be used to measure with precision the voltage across, or electrical currents passing through, neuronal or other cellular membranes by inserting an electrode inside the neuron.

Example 14. Electrowetting Technique and Nanobiopsy Application

The microneedles and micropipettes provided herein are suitable for use in nanobiopsy platforms to extract samples from the soma of living cells.

Example 15. Microscopy Techniques

The microneedles provided herein are suitable for use in a wide range of microscopic techniques. For example, the microneedles may be used in scanning electrochemical microscopy (SECM) to obtain topographic information of non-conducting surfaces.

In another embodiment, the microneedles may be used in scanning ion conductance microscopy (SICM), a type of scanning probe microscopy (SPM), to measure the local electrochemical behavior of liquid/solid, liquid/gas and liquid/liquid interfaces. SECM may be employed to probe the topography and surface reactivity of solid-state materials, track the dissolution kinetics of ionic crystals in aqueous environments, screen electrocatalytic prospects, elucidate enzymatic activities, and investigate dynamic transport across synthetic/natural membranes and other biophysical systems.

In biological systems, the ability to probe non-conductive surfaces makes SECM a feasible method for analyzing membranes, redox active enzymes, and other biophysical systems. Changes in intracellular redox activity may be related to conditions such as oxidative stress and cancer. Redox processes of individual living cells can be probed by SECM, which serves as a non-invasive method for monitoring intracellular charge transfer.

In other aspects, the microneedles provided herein may be used in near-field scanning optical microscope (NSOM) techniques for nanostructure investigation. This technique surpasses the far field resolution limit by exploiting the properties of evanescent waves. In NSOM, excitation laser light is focused through an aperture with a diameter smaller than the excitation wavelength, resulting in an evanescent field (or near-field) on the far side of the aperture.

Example 16. Nanospray Mass Spectrometry/Nanoelectrospray/a Minimized-Flow Electrospray Ionization Source Nanospray uses gold coated glass microneedles. The techniques provided herein may be used to visualize the tips of these microneedles. Additionally, the techniques provided herein may be beneficial in techniques involving capillary electrophoresis/electrospray-mass spectrometry in peptide analysis and peptidomics. The non-adhesive coating helps ensure that molecules to be analyzed by the system are not retained in the micropipette, and the color marking may aid in visualization of the tip of the microneedle.

Example 17. Tapered Optical Fibers

In other aspects, optical fibers, which cover a given length, may be stretched out to very small diameters. Capillary optical fiber (COF) is a type of optical fiber with a central air hole, a $GeO_2$—$SiO_2$ ring core, and $SiO_2$ cladding. For example, diabatic tapers are shown at the following link (see, https://www.aflglobal.com/Products/Fusion-Splicing/Specialty-Fiber-Optic-Components-and-Services/Adiabatic-Tapers.aspx). The color marking techniques provided herein may be applied to optical fibers to improve visualization of the tips of these fibers.

Example 18. Micropipette Aspiration

Micropipette aspiration a technique in which micropipettes are used to perform mechanical measurements and manipulations of single cells. Micropipette aspiration has been applied to a variety of experimental systems that span different length scales to study cell mechanics, nanoscale molecular mechanisms in single cells, bleb growth, and nucleus dynamics. Further technical advancements of microfluidics-based micropipette aspiration will have broad applications in both fundamental cell mechanics studies and for disease diagnostics. The micropipettes provided herein are compatible with aspiration studies.

Example 19. Deep Brain Injections/Convection Enhanced Delivery

This technique may target deep brain structures with microinjections using microneedles for delivery of drugs, viral vectors, or cell transplants. Microinjection with a glass capillary tube represents a significant improvement in injection techniques and deep brain targeting with minimal collateral damage.

Example 20. Inducible Materials

The microneedles provided herein may be used in systems which provide a source of biological components or inducible materials in the tip of the needle. When the microneedle is inside the cell, biological processes can be triggered or induced by flow of these components into the interiors of the cell. These techniques apply for both glass microneedles and 3D fabricated needles.

What is claimed is:

1. A micropipette or microneedle comprising:
a tubular region of substantially constant outer diameter having a distal end and a distally tapered tip region projecting from the distal end of the tubular region, wherein the tubular region is longer than the distally tapered tip region;
a high contrast color marking located at a distal end of the micropipette or the microneedle;
wherein the micropipette or the microneedle has an outer surface and an inner surface with the color marking on the outer surface, and the color marking comprising one or more color marking reagents suitable for visualizing the micropipette or the microneedle by a microscope;
wherein the one or more color marking reagents adhere to the outer surface of the micropipette or the microneedle;
wherein the one or more color marking reagents comprises nanoparticles, and wherein the nanoparticles are modified to minimize binding of biological material to the micropipette or the microneedle from adsorption of proteins and other cellular components.

2. The micropipette or microneedle of claim 1, wherein the nanoparticles are selected from the group consisting of: gold nanoparticles (AuNPs), gold-silver nanoparticles (AuAgNPs), or a combination thereof.

3. The micropipette or the microneedle of claim 1, further comprising an anti-adhesive reagent and an anti-clogging reagent,
wherein the anti-adhesive reagent adheres to the inner surface, and
wherein the anti-clogging reagent adheres to the outer surface.

4. The micropipette or the microneedle of claim 1, wherein a length of the color marking covers about 1 to 100% of a length of the micropipette or a microneedle.

5. The micropipette or the microneedle of claim 1, wherein the color marking is in a form of a pattern, applied during an additive printing process or generated by a cured photomaterial manufacturing process, and wherein microstructures are present on the inner surface of the micropipette or the microneedle.

6. The micropipette or the microneedle of claim 5 wherein the high contrast color marking comprises an additive to the cured photomaterial.

7. The micropipette or the microneedle of claim 1 wherein the tip region comprises a sharp-pointed tip of 3D-printed cured photomaterial.

8. The micropipette or the microneedle of claim 7 wherein the tip region has one or more side openings.

9. The micropipette or microneedle of claim 1 wherein the tip region has a closed distal end.

10. The micropipette or the microneedle of claim 1 wherein the micropipette or the microneedle has an inner diameter in the range of about 0.2 microns to 1.56 mm.

11. A micropipette or microneedle comprising:
a high contrast color marking located at an end of the micropipette or the microneedle,
wherein the micropipette or the microneedle has an outer surface and an inner surface, with the color marking on the outer surface, and the color marking comprising one or more color marking reagents suitable for visualizing the micropipette or the microneedle by a microscope, and wherein the one or more color marking reagents adhere to the outer surface of the micropipette or the microneedle,
further comprising an anti-adhesive reagent and an anti-clogging reagent,
wherein the anti-adhesive reagent adheres to the inner surface, wherein the anti-clogging reagent adheres to the outer surface, wherein a modification is made to the anti-clogging reagent, wherein the modification comprises attaching a first end of a cross-linker to the anti-clogging reagent and a second end of the cross-linker to the color marking reagent to form a cross-linked reagent and attaching the cross-linked reagent to the outer surface.

12. The micropipette or microneedle of claim 11 further comprising a tubular region of substantially constant outer diameter having a distal end and a distally tapered tip region projecting from the distal end of the tubular region, wherein the tubular region is longer than the distally tapered tip region.

13. The micropipette or microneedle of claim 12 wherein the micropipette or microneedle comprises 3D-printed cured photomaterial.

* * * * *